(12) United States Patent
Gough

(10) Patent No.: US 6,241,875 B1
(45) Date of Patent: Jun. 5, 2001

(54) METHOD OF PROVIDING HEAT

(75) Inventor: Arthur Gough, Northallerton (GB)

(73) Assignee: BG plc, Berkshire (GB)

( * ) Notice: Subject to any disclaimer, the term of this patent is extended or adjusted under 35 U.S.C. 154(b) by 0 days.

(21) Appl. No.: 09/355,324

(22) PCT Filed: Jan. 30, 1998

(86) PCT No.: PCT/GB98/00299

§ 371 Date: Oct. 21, 1999

§ 102(e) Date: Oct. 21, 1999

(87) PCT Pub. No.: WO98/33587

PCT Pub. Date: Aug. 6, 1998

(30) Foreign Application Priority Data

Feb. 1, 1997 (GB) .................................................. 9702114

(51) Int. Cl.[7] .................................................. C10G 31/06
(52) U.S. Cl. ........................ 208/106; 208/46; 165/134.1; 60/670
(58) Field of Search .............................................. 208/106

(56) References Cited

U.S. PATENT DOCUMENTS

| | | | |
|---|---|---|---|
| 2,877,000 | * 3/1959 | Person | 257/245 |
| 4,173,254 | * 11/1979 | Paull et al. | 165/134 R |
| 4,178,758 | * 12/1979 | Paull et al. | 60/648 |
| 4,364,726 | 12/1982 | Forster et al. | 431/215 |
| 4,582,129 | * 4/1986 | Yano et al. | 165/97 |
| 5,097,819 | * 3/1992 | Talbert et al. | 126/110 R |
| 5,270,127 | * 12/1993 | Koga et al. | 429/17 |

FOREIGN PATENT DOCUMENTS

| | | | |
|---|---|---|---|
| 42 02 107 A1 | * 7/1993 | (DE) | . |
| 0 408 751 A1 | * 1/1991 | (EP) | . |
| 0 529 329 A2 | * 3/1993 | (EP) | . |
| 0 601 270 | 6/1994 | (EP) | . |

OTHER PUBLICATIONS

PCT/GB98/00299, International Search Report, May 1998.*
PCT/GB98/00299, International Preliminary Examination Report, Oct. 1998.*

* cited by examiner

Primary Examiner—Ellen M. McAvoy
(74) Attorney, Agent, or Firm—Oblon, Spivak, McClelland, Maier & Neustadt, P.C.

(57) ABSTRACT

A heat exchanger formed of two plates or stages with one being on top of the other and with a plurality of such heat exchangers stacked on each other. The first stage has an inlet opening, an inlet passage and passages opened to the end of the stage. The second stage has an inlet opening leading to passages which lead to an outlet passage and an outlet opening. The second stage also has an inlet opening leading to passages which have an outlet at the end. A combustible gas enters the passage region of the first stage where the mixture is preheated and then passes to a passage region of the first stage. Portions of the gas passages in the passage region contain a combustion promoting catalyst so that the gas burns in the passage region. The products of combustion leave through the outlet end and are conveyed to an inlet of the passage region of the second stage.

19 Claims, 2 Drawing Sheets

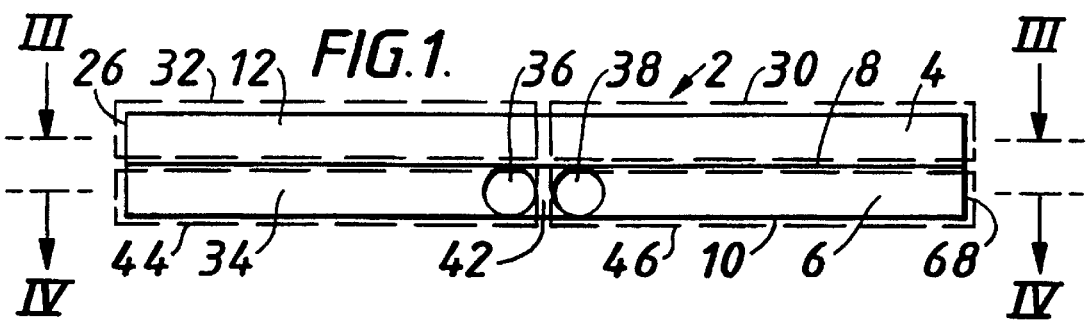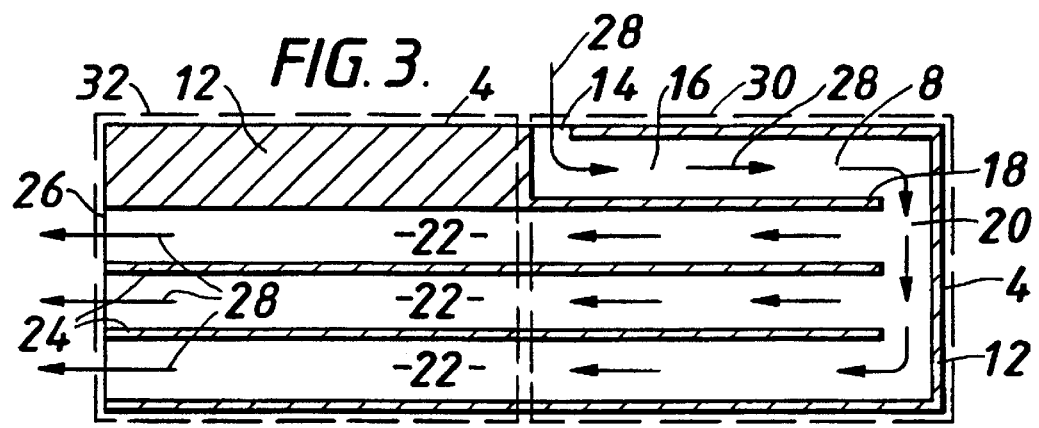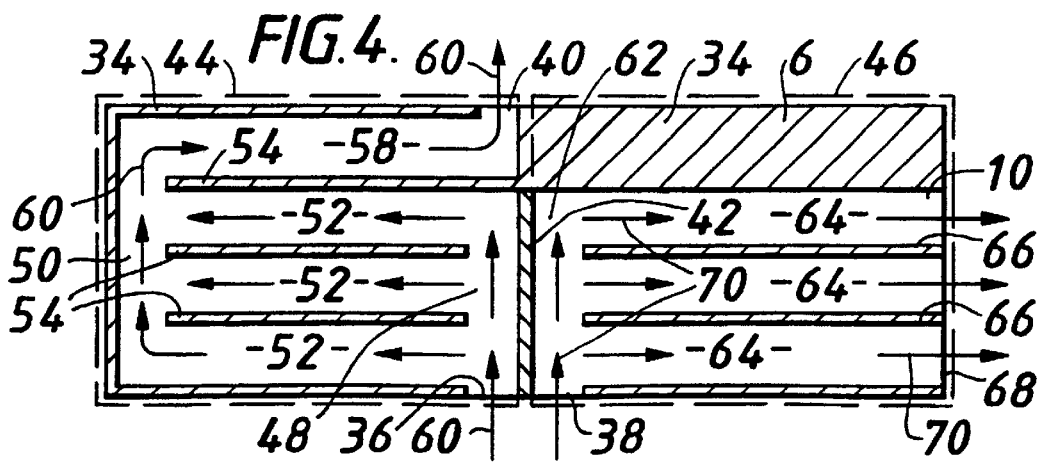

METHOD OF PROVIDING HEAT

This invention relates to a method of providing heat to promote an endothermic reaction or be extracted as sensible heat.

SUMMARY OF THE INVENTION

BACKGROUND OF THE INVENTION

Field of the Invention

According to the invention there is provided a method of providing heat to promote an endothermic reaction or be extracted as sensible heat, the method comprising providing first passage means having first inlet means thereto and first outlet means therefrom, when considering fluid flow along said first passage means towards the first outlet means from the first inlet means said first passage means having an upstream portion leading towards a downstream portion of said passage means, second passage means having second inlet means thereto and second outlet means therefrom, third passage means having third inlet means thereto and third outlet means therefrom, heat conducting wall means provided between said upstream portion of the first passage means and the second passage means and between said downstream portion of the first passage means and the third passage means, introducing combustible gas and oxidant into the upstream portion of the first passage means wherein said fuel gas and oxidant are heated by heat conducted through said wall means from the second passage means, burning the combustible gas with said oxidant in said downstream portion of the first passage means, supplying the resultant products of combustion to the second inlet means to the second passage means for said products of combustion to flow along the second passage means to said second outlet means wherein the products of combustion give up heat which is conducted through said wall means to said upstream portion of the first passage means to heat further introduced said combustible gas and oxidant, and either (i) introducing one or more fluid substances into the third passage means through the third inlet means to undergo an endothermic chemical reaction using heat conducted through said wall means from said downstream portion of the first passage means such that products of the reaction leave through said third outlet means or (ii) introducing an heatable fluid into the third passage means to receive heat conducted through said wall means from said downstream portion of the first passage means such that the heatable fluid becomes heated and thereafter leaves through the third passage means bearing sensible heat.

BRIEF DESCRIPTION OF THE DRAWINGS

The invention will now be further described, by way of example, with reference to the accompanying drawings in which:

FIG. 1 is a diagramatic side elevation of an heat exchanger stage comprising two plates, for use in carrying out the method according to the invention, FIG. 2 is a diagramatic elevation from the opposite side of the heat exchanger stage in FIG. 1, FIG. 3 is a diagramatic section on line III—III in FIG. 1 showing one of the plates in section, FIG. 4 is a diagramatic section on line IV—IV in FIG. 1 showing the other plate in section.

DETAILED DESCRIPTION OF THE PREFERRED EMBODIMENTS

Figure 5:
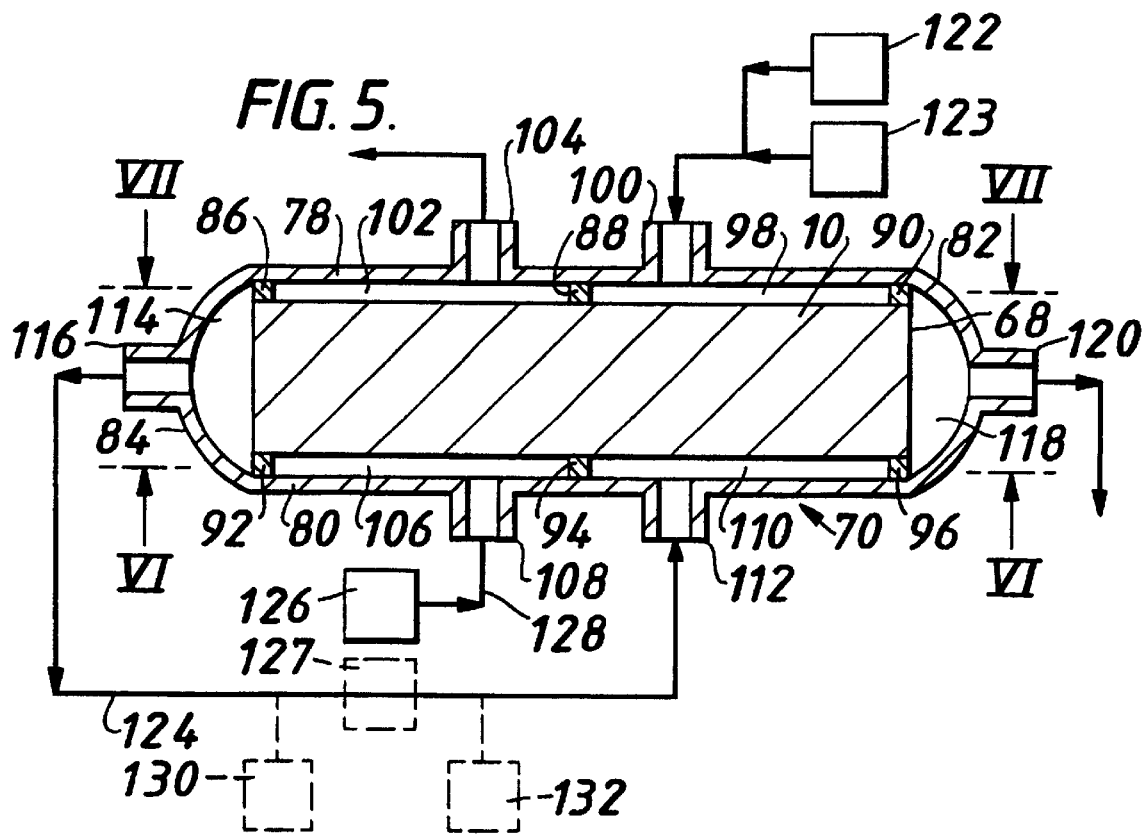
FIG. 5 shows diagramatically and partly in cross-section, apparatus for carrying out the method according to the invention comprising a plurality of the heat exchangers in FIG. 1, the part section in FIG. 5 being on line V—V in FIG. 6.

With reference to the accompanying drawings a heat exchanger 2 is formed by a pair of plate-like stages 4 and 6 which may be of rectangular form as shown. Each stage 4 and 6 is initially of open top form and has a respective base 8 or 10. The stage 4 has a peripheral wall 12 around three of its sides with an inlet opening 14 leading to an inlet passage 16, in part defined by a wall 18, leading to a manifold region 20 from which passages 22, defined at least in part by walls 24, lead to an open side 26 of stage 4. A flow of fluid through stage 4 can follow the path(s) indicated by arrows 28 from the inlet opening to an outlet at the open side 26. For the purpose of the explanation below, the passages in the stage 4 may be considered as being formed by a passage portion 30 and a passage portion 32 each generally demarcated or indicated by phantom lines. With respect to the direction of fluid flow 28, the passage portion 30 is an upstream portion and the passage portion 32 is a downstream portion. The stage 6 has a peripheral wall 34 around three of the sides of the base 10, the wall having inlet openings 36 and 38 and an outlet opening 40. The stage 6 is divided substantially in half by a wall 42 to one side of which is a passage portion 44 demarcated or indicated by phantom lines and to the other side of which is a passage portion 46 demarcated or indicated by further phantom lines. The passage portion 44 comprises manifold regions 48 and 50 between which extend passages 52 defined at least in part by walls 54, and from the manifold 50 an outlet passage 58 extends to the outlet opening 40. A flow of fluid through the passage portion 44 can follow the path(s) indicated by arrows 60. The passage portion 46 comprises an inlet manifold region 62 from which lead passage 64, defined at least in part by walls 66, to an open side 68 of the stage 6. A flow of fluid through the passage portion 46 can follow the path indicated by arrows 70.

The stages 4 and 6 may be formed from any suitable heat conducting material for example metal, which may be stainless steel, or ceramic material. Ceramic material may be moulded to form the stages 4 and 6 as may be metal. Or metal block may be etched, ground or otherwise machined or cut to form the stages 4 and 6. Or the stages 4 and 6 may be formed from component parts of sheet or strip material adhered together in a substantially fluid light manner, for example by brazing or welding in the case of sheet or strip metal.

As indicated in FIGS. 1 and 2, a heat exchanger 2 is formed by mounting a said stage 4 on top of said stage 6 in a fluid tight manner whereby the upper wall of the passages 52, 58, 64 and regions 48, 50 and 62 and regions 48, 50 and 62 is formed by the base 8 of the stage 4.

Preferably a plurality of heat exchangers 2 are stacked one on top of another, the uppermost stage 4 in the stack being provided with a suitable cover to form an upper wall of the passages 16, 22 and region 20 in that uppermost stage 4; each lower stage 4 in the stack being covered by a respective base 10 of an aforesaid stage 6 directly above that stage 4.

Figure 6:
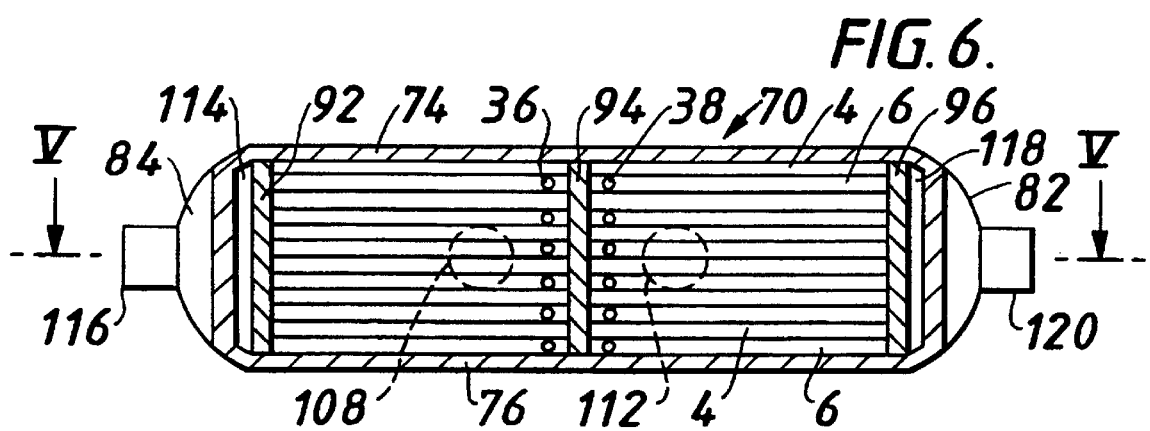
FIG. 6 is a diagramatic section on line VI—VI in FIG. 5.
Figure 7:
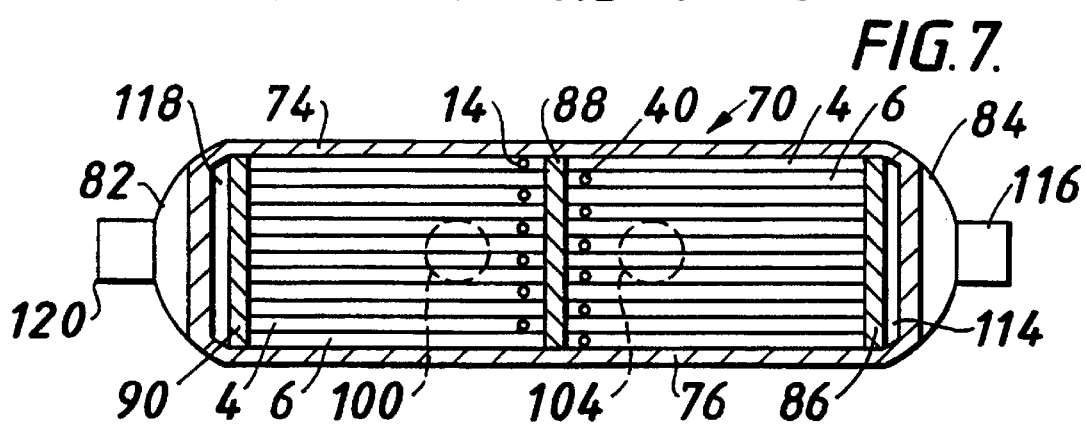
FIG. 7 is a diagramatic section on line VII—VII in FIG. 5.

A stack of heat exchangers 2 is shown in FIGS. 5 to 7 inside a containment shell or pressure vessel 70 having flat top and bottom walls 74 and 76, curved side walls 78 and 80, and hemispherical end walls 82 and 84. The top wall 74 of the pressure vessel 72 forms the upper wall for the passages and region in the uppermost stage 4, whilst the base 10 (FIGS. 1 and 4) of the lowermost stage 6 in the stack sits on the bottom wall 76 of the vessel. Fluid tight, spaced partitions 86, 88, 90 and 92, 94, 96 extend down both sides of the stack. A region 98 between the partitions 88 and 90 serves as inlet manifold to the inlet openings 14 in the stages 4; the inlet manifold 98 having an inlet 100 thereto. A region 102 between partitions 86 and 88 serves as an outlet manifold for the outlet openings 40 in the stages 6; the outlet manifold 102 having an outlet 104 therefrom. A region 106 between the partitions 92 and 94 serves as an inlet manifold for the inlet openings 36 in the stages 6; the inlet manifold 106 having an inlet 108 thereto. A region 110 between the partitions 94 and 96 serves as an inlet manifold for the inlet openings 38 in the stages 6; the inlet manifold 110 having an inlet 112. Between the partitions 86 and 92 and the end wall 84 of the pressure vessel 70 is a region 114 serving an outlet manifold for the outlet openings at the open sides 26 (FIGS. 1, 2 and 3) of the stages 4; the outlet manifold 114 having an outlet 116. Between the partitions 90 and 96 and the end wall 82 of the pressure vessel 70 is a region 118 serving as an outlet manifold for the outlet openings at the open sides 68 (FIGS. 1, 3, 4 and 5) of the stages 6; the outlet manifold having an outlet 120.

A fuel or combustible gas, for example natural gas or methane, from a suitable supply 122 and oxidant, for example air or oxygen, from a suitable supply 123 are fed to the inlet 100 at a temperature below the ignition temperature of the combustible gas/oxidant mixture for the mixture to be heated (in a manner to be described below) in the passage portion 30 of each stage 4. The passages 16, 20, 22 in the stages 4 may be of sufficiently small dimensions to prevent propagation of flames. Alternatively or additionally the gas velocity may be maintained sufficiently high to prevent backward propagation of combustion. From the passage portions 30 in stages 4 the heated combustible gas/oxidant mixture continues along the passages 22 in the passage portions 32 of the stages 4 where combustion of the mixture is promoted by suitable catalyst means in those parts of the passages 22 in the passage portion 32. The catalyst means may be provided in particle or granular form or in the form of a coating on walls of the passages 22. The combustion products enter outlet manifold 116 from whence they are carried via ducting 124 to inlet 112 from which they pass via manifold 110 into the passages 64 (FIG. 4) of the stages 6 and then leave through the outlets 68 (FIGS. 4 and 5) to the manifold 118 for exit through the outlet 120. Heat from the products of combustion in the passage portions 46 of the stages 6 transfers across the bases 8 to the incoming mixture of combustible gas and oxidant to heat the mixture. Heat from the gases leaving the outlet 120 may be recovered by means of suitable heat exchange means.

A stream of fluid, from a suitable supply 126, capable absorbing heat, preferably a large proportion of heat, generated in the passage portions 32 of the stages 4 is supplied via ducting 128 into the passage portions 44 of the stages 6 via the manifold 106 and leaves via the manifold 102 and outlet 104 for collection and/or further processing. The fluid supplied by supply 126 may be a substance or mixture of substances, and may be liquid or gaseous, which can undergo an endothermic chemical reaction, or the fluid may remove the heat conducted across the bases 8 of the passage portions 32 of the stages 4 as sensible heat. Examples of suitable endothermic reactions are dehydrogenation of at least one hydrocarbon (for example, ethane or propane or butane or a mixture comprising at least two of those) to at least one olefine or diene, dehydrogenation of one or more paraffins, conversion of hydrocarbons to aromatics, and steam reforming of hydrocarbons, for example substantially methane, to produce hydrogen and oxides of carbon. To promote these reactions suitable catalyst means may be provided in the passage portions 44 of the stages 6; this catalyst means may be provided in particle or granular form or in the form of a coating on the walls of the passages 48, 52, 58, 60 (FIG. 4). An alternative endothermic reaction may be, in the absence of catalyst means, thermal cracking of hydrocarbons to produce olefines, for example conversion of ethane, propane or other paraffins to ethylene and other products. An example of removing the heat as sensible heat is the raising of steam in the passage portions 44 in the stages 6 from water supplied to inlet manifold 106, though other fluids besides water may be used and need not be vapourised.

The passages 52, 58 and region 48, 62 in the stages 6 (FIG. 4) may be deeper or shallower than passages 16, 22 and regions 20 in the stages 4 (FIG. 3) to provide more or less residence time for conducting the desired reactions.

The products of combustion conveyed by the ducting 124 may be subject to treatment in external treatment means 127 which may be an adiabatic catalyst zone to complete the combustion of the combustible gas and/or an heat exchanger to vary the temperature of the gas entering inlet 112. Means 130 and 132 may be provided for adding gas to the ducting 124 or removing gas therefrom. By one or more of these arrangments the gas in the ducting 124 supplied to the inlet 112 may be at the appropriate temperature to provide the desired amount of preheat to the combustible gas and oxidant supplied through inlet 100. In particular adding hot gas to the duct 124 by means 130 or 132 and, if desired, varying or reducing the flow of combustible gas and oxidant through the passages 22 can provide a convenient mode of heating the passage portions 30 in the stages 4 at start up.

In the arrangement described with reference to FIGS. 3 and 4 the fluid in passages 52 flows in co-current with the flow in passages 22. However by using the opening 104 as an inlet and the opening 108 as an outlet, the fluid flow in the passages 52 can be opposite to that of the arrows 60 and thus in counter-current to the flow in the passages 22.

The skilled addressee will easily understand that the passages 52, 58 can be disposed transversely or cross-wise to the direction of the passages 22.

The apparatus disclosed has the following advantages:

(A) The stages 4 and 6 may be constructed of materials which do not have the mechanical strength to fully withstand the pressure difference between the atmosphere and the pressure inside the stages 4 and 6. The material inside the vessel 70 merely has to withstand pressure diferences between the passage portions 44 and those prevailing in passage portions 30, 32, 46 and those pressure differences may be kept small.

(B) Combustion products in the manifolds 114 and 110 can be outside flamable limits so leaks to atmosphere will not be dangerous.

(C) The mixing of the combustible gas and oxidant can be carried out at relatively low temperature and then the mixture is conveyed along the passages 22 to the combustion regions formed by the passage portions 32 where the combustion temperatures are reached; the passages 22 in the passage portions 30 may be narrow to form a flame trap.

(D) The endothermic reaction carried out the passage portions 44 may remove heat rapidly from the combustion regions in the passage portions 30 so that high combustion temperatures which promote formation of $NO_x$ need not be reached.

If desired the pressure vessel 70 may be omitted. In this case the stages 4 and 6 will have to be formed of suitable pressure resistant material, and appropriate folds provided instead of the regions 98, 102, 106, 110, 114 and 118.

What is claimed is:

1. A method of providing heat to promote an endothermic reaction or be extracted as sensible heat, the method comprising providing a first passage having a first inlet thereto and a first outlet therefrom, when considering fluid flow along said first passage towards the first outlet from the first inlet said first passage having an upstream portion leading towards a downstream portion of said first passage, a second passage having a second inlet thereto and a second outlet therefrom, a third passage having a third inlet thereto and a third outlet therefrom, a heat conducting wall provided between said upstream portion of the first passage and the second passage and between said downstream portion of the first passage and the third passage, introducing combustible gas and oxidant into the upstream portion of the first passage wherein said combustible gas and oxidant are heated by heat conducted through said wall from the second passage, burning the combustible gas with said oxidant in said downstream portion of the first passage, supplying the resultant products of combustion to the second inlet to the second passage for said products of combustion to flow along the second passage to said second outlet wherein the products of combustion give up heat which is conducted through said wall to said upstream portion of the first passage to heat further introduced said combustible gas and oxidant, and either (i) introducing one or more fluid substances into the third passage through the third inlet to undergo an endothermic chemical reaction using heat conducted through said wall from said downstream portion of the first passage such that products of the reaction leave through said third outlet or (ii) introducing a heatable fluid into the third passage through the third inlet to receive heat conducted through said wall from said downstream portion of the first passage such that the heatable fluid becomes heated and thereafter leaves through the third passage bearing sensible heat.

2. A method as claimed in claim 1, in which combustion promoting catalyst is disposed in said downstream portion of said first passage.

3. A method as claimed in claim 1, in which said combustible gas is natural gas.

4. A method as claimed in claim 1, in which the first passage is formed in a first stage, the second and third passage are formed in a second stage, the first and second stages are mounted one on another to form a heat exchanger, and a plurality of said heat exchangers are stacked one on another.

5. A method as claimed in claim 4, in which said heat exchangers are disposed in a pressure vessle.

6. A method as claimed in any one of claims 1 to 3, in which, between the first passage and the second passage, the products of combustion pass through a heat exchanger.

7. A method as claimed in claim 1, in which, between the first passage and the second passage, the products of combustion from the first passage are subject to further combustion.

8. A method as claimed in claim 1, in which products of combustion are extracted from the flow of said products to the second passage.

9. A method as claimed in claim 1, in which at least one gas is added to the products of combustion being supplied to the second passage.

10. A method as claimed in claim 1, in which walls of said first, second and third passage are formed of ceramic material.

11. A method as claimed in claim 1, in which the endothermic reaction is the steam reforming of at least one hydrocarbon to produce hydrogen and oxides of carbon.

12. A method as claimed in claim 11, in which the hydrocarbon is substantially methane.

13. A method as claimed in claim 1, in which the endothermic reaction is thermal cracking of at least one hydrocarbon to produce at least one olefine or at least one diene.

14. A method as claimed in claim 13, which the hydrocarbon is ethane or propane or butane, or there is more than one hydrocarbon and the mixture comprises at least two members of the group consisting of ethane, propane and butane.

15. A method as claimed in claim 1, in which the endothermic reaction is dehydrogenation of a paraffin.

16. A method as claimed in 1, in which the heatable fluid is water converted in the third passage to steam exhibiting said sensible heat.

17. A method as claimed in claim 2, in which said combustible gas is natural gas.

18. A method as claimed in claim 2, in which the first passage is formed in a first stage, the second and third passage are formed in a second stage, the first and second stages are mounted one on another to form a heat exchanger, and a plurality of said heat exchangers are stacked one on another.

19. A method as claimed in claim 3, in which the first passage is formed in a first stage, the second and third passage are formed in a second stage, the first and second stages are mounted one on another to form a heat exchanger, and a plurality of said heat exchangers are stacked one on another.

* * * * *